United States Patent [19]

Phillips et al.

[11] Patent Number: 5,475,235
[45] Date of Patent: Dec. 12, 1995

[54] CONTROL OF LASER LIGHT POWER OUTPUT FOR USE IN LIGHT SCATTERING INSTRUMENTS BY INDUCING MODE HOPPING AND AVERAGING RESULT

[75] Inventors: David T. Phillips, Goleta; Gary R. Janik, Santa Barbara, both of Calif.

[73] Assignee: Wyatt Technoloy Corporation, Santa Barbara, Calif.

[21] Appl. No.: 105,200

[22] Filed: Aug. 9, 1993

[51] Int. Cl.⁶ ................................................. G01N 15/06
[52] U.S. Cl. ........................................... 250/574; 356/343
[58] Field of Search ............................ 250/574; 356/337, 356/338, 340, 343

[56] References Cited

U.S. PATENT DOCUMENTS

| | | | |
|---|---|---|---|
| 3,815,045 | 6/1974 | Ito . | |
| 4,146,799 | 3/1979 | Pitt et al. | 250/574 |
| 4,420,256 | 12/1983 | Fladda et al. | 356/336 |
| 4,616,927 | 10/1986 | Phillips et al. . | |
| 5,121,988 | 6/1992 | Blesener et al. | 356/442 |

FOREIGN PATENT DOCUMENTS

4133772A1  5/1992  Germany .

OTHER PUBLICATIONS

D. L. Ojima et al., Diode laser noise at video frequencies in optical video disk players, Applied Optics vol. 25, No. 9, May 1, 1986.

J. Vanderwall and J. Blackbum, Suppression of some artifacts of modal noise in fiber, optic systems, Optics Let. vol. 4, No. 9, pp. 295–296, Sep. 1979.

K. Stubjkaer and M. Small, Feedback–induced noise in index–guided semiconductor lasers and its reduction by modulation, Electronics Let. vol. 19, pp. 388–399 (1983).

E. Gage and S. Beckens, Effects of high frequency injection and optical feedback on semiconductor laser performance, *Optical Data Storage*, SPIE vol. 1316, pp. 199–204 (1990).

P. J. Wyatt, Light scattering and the absolute characterization of macromolecules, Analytica Chimica Acta vol. 272, pp. 1–40 (1993).

*Primary Examiner*—David C. Nelms
*Assistant Examiner*—Steven L. Nichols
*Attorney, Agent, or Firm*—Philip J. Wyatt

[57] ABSTRACT

The incorporation of certain classes of solid state lasers into light scattering instrumentation is desirable because of their compact structure. However, mode hopping often causes the output power produced by such lasers to be unstable. The frequency of such output power fluctuations is often so broad that output power monitoring means, characteristic of the light scattering instrumentation into which such lasers are incorporated, cannot track accurately the temporal output power fluctuations. A method, and associated apparatus, is described whereby the laser drive current is modulated at low frequency and amplitude sufficient to induce and thereby control mode hopping so as to permit accurate measurement of the ratio of light scattering signals to the laser output power.

26 Claims, 4 Drawing Sheets

CONTROL OF LASER LIGHT POWER OUTPUT FOR USE IN LIGHT SCATTERING INSTRUMENTS BY INDUCING MODE HOPPING AND AVERAGING RESULT

REFERENCES CITED

U.S. Pat. No. 3,815,045 (1974), Ryoichi Ito

German Patent DE 41 33 772 A1 (1992), M. Kohno and J. Itami

U.S. Pat. No. 4,616,927 (1986) (Light Scattering Flow cell)

J. Vanderwall and J. Blackburn, Optics Let. Vol. 4, No. 9, pp 295–296, September 1979

K. Stubkjaer and M. Small, Electronics Let. Vol. 19, pp 388–399 (1983)

L. Ojima et al., Applied Optics Vol. 25, No. 9, 1 May 1986

E. Gage and S. Beekens, *Optical Data Storage*, SPIE Vol. 1316, pp 199–204 (1990)

P. J. Wyatt, Analytica Chimica Acta Vol 272, pp 1–40 (1993).

RELATED PATENTS CITED

As this invention is concerned with the use of certain classes of lasers for light scattering measurements, the following U.S. patents are related to such measurements and are incorporated by reference herein:

U.S. Pat. No. 4,541,719 (Sep. 17, 1985) *Method and Apparatus for Characterizing Micro Particles and Measuring Their Response to Their Environment*

U.S. Pat. No. 4,548,500 (Oct. 22, 1985) *Process and Apparatus for Identifying or Characterizing Small Particles*

U.S. Pat. No. 4,693,602 (Nov. 6, 1984) *Method and Apparatus for Measuring the Light Scattering Properties of Small Particles*

U.S. Pat. No. 4,710,025 (Dec. 1, 1987) *Process for Characterizing Suspensions of Small Particles*

U.S. Pat. No. 4,907,884 (Mar. 13, 1990) *Sample Cell Monitoring System*

U.S. Pat. No. 5,129,723 (Jul. 14, 1992) *High Performance Zimm Chromatography*

U.S. Pat. No. Des. 329,821 (Feb. 21, 1989) *Apparatus for the Measurement of Fine Particles in Liquid Suspension by the Light Scattering Procedure*

BACKGROUND AND PRIOR ART

Careful measurement of light scattered from molecules and from small particles in solution is a convenient and versatile laboratory technique for determining their various physical characteristics, such as molecular weights and sizes and, similarly, particle size and structure. Combined with various chromatographic separation devices and concentration detectors, such light scattering measurements also permit the deduction of the differential distributions of these quantities. A detailed review of light scattering measurements, requirements for their performance, and results that may be derived are found in the review article by Wyatt cited above. Because laboratory space is limited and expensive, compact instrument designs are favored. The need for compact design makes the use of the very small semiconductor diode laser light source more desirable than the larger gas laser light source. However, the semiconductor diode laser presents a number of problems that must be overcome for practical use in light scattering instruments and detectors.

Among these problems is the sudden change of power level due to mode-hopping. Small changes in the operating conditions of the laser can produce sudden changes in the operating power of the laser as the dominant oscillation moves from one mode to another. This effect can be caused by small changes in temperature, drive current, or light reflected back into the laser. Changes in reflected light are a natural part of the light scattering measurement since the introduction of a sample causes additional light to be scattered back into the laser and the changing refractive index of the solution also varies the phase of the scattered light. Additional light may be reflected into the laser from the regions of the sample cell where the laser beam enters and exits. Preventing this scattered and reflected light from interacting with the laser requires expensive additional components. For extremely complex sample holding structures such as the flow cell described in U.S. Pat. No. 4,616,927, the large number of parallel surfaces mounted perpendicularly to the incident laser beam renders the complete removal of back reflected components almost impossible. When the temperature and drive current are at the critical point for a mode shift, small random changes in the reflected light level and phase can cause the laser power to fluctuate rapidly up and down by several percent.

The essential physical property measured by a light scattering instrument, or more commonly a light scattering photometer, is the ratio of the light power incident on the sample per unit area to the light power scattered by the sample per steradian. If the laser light source were perfectly stable, the incident power need be measured only once, as a calibration procedure. Unfortunately, the laser power tends to change with temperature, reflected light, drive current, and age. The conventional approach for dealing with changes in laser power is to split off part of the beam and use it to monitor the laser power with an optical detector. The laser monitor signal thus produced may be used either to stabilize the laser power, by providing feedback for an electronic circuit that will adjust the drive current, or to normalize the scattered light signal during mathematical processing of the measured data. In either case, the effect is to divide the scattered light signal by the laser monitor signal. Both of these approaches, however, can still result in small errors. Laser mode-hopping may occur very rapidly, resulting in a change of laser power for a short time, until the monitor feedback signal and control circuitry can adjust the drive current to restore the desired power level. Similarly, a lack of simultaneity or signal averaging symmetry in the measurement of the scattered light detector signal and the laser monitor detector signal can result in significant error if the signals change too rapidly for the monitor to follow. Another source of error is that the laser beam may consist of more than one spatial and temporal component, or beamlet. The laser monitor may respond to a different combination of these beamlets than do the light scattering detectors, thus preventing the monitor from accurately tracking a signal proportional to the scattering signals. For all these masons, it is desirable to avoid the sudden, often high frequency, laser power changes that are caused by mode-hopping.

Diode laser mode hopping noise in optical and communication signal applications occurs at very high frequencies and has been the subject of many research reports and several patents. This very high frequency noise is particularly wordsome in communications applications since it occurs at frequencies comparable to the desired communications signal frequencies themselves. For the case of light scattering measurements generally performed at very low frequencies, it is only necessary for the average scattering detector signal and the average monitor signal to track accurately. The reduction of high frequency mode hopping noise by the use of a 2.5 GHz drive current modulation was reported in the reference by J. Vanderwall and J. Blackburn cited earlier. Also as cited earlier, the reduction of noise in a video disk system by drive modulation at over 100 MHz was reported by Hitachi engineers M. Ojima and S. Yonezawa. IBM engineers K. Stubkjaer and M. Small reported noise reduction using 50 to 200 MHz modulation. Further cited work by Ojima et al. used modulation at 200 MHz to 1 GHz. The optimum modulation drive frequency for high frequency noise reduction was shown to be related to the time delay of light reflected back into the laser, in the cited work by E. Gage and S. Beckens. Modulation drive frequencies of 100 to 450 MHz were studied. In addition, these studies used very high levels of modulation, actually running the drive current below threshold during part of the modulation cycle, and, presumably, shutting off coherent emissions during that period.

In the cited U.S. patent by Ryoichi Ito, assigned to Hitachi, U.S. Pat. No. 3,815,045 (1974), "Method of and Device for Modulating Directly a Semiconductor Laser", the use of a modulated drive current to shift a semiconductor laser between two spatially distinct modes is described, which results in a high frequency modulation of the output beam by optically selecting only one of the spatial modes. This method is not applicable to light scattering photometers because light scattering photometers require stabilized light beams, rather than modulated light beams. The most satisfactory lasers for light scattering instruments operate in only one spatial mode in order to ensure a collimated beam. Operation in other spatial modes as described by Ito would exacerbate stray light problems.

Japanese patent application SHO 59 9086 and its corresponding German application DE 41 33 772 A1 (May 21, 1992) by M. Kohno and J. Itami, assigned to Mitsubishi, describe a particular compact disc reading detector structure in which reflected light causes noise which is best reduced by modulation at 500 to 600 MHz. The optimal frequency selected is based on the distance of the laser source from the reflecting region of the disc. This concept is not applicable to light scattering instruments for several reasons: First, the use of 500 MHz drive current is expensive and inconvenient. Second, because the light scattering sample material is often carried along or through the laser beam by fluid flow, there is no fixed scattering distance, and therefore no single optimum high frequency of modulation. Third, very high frequency noise reduction is of little importance in a light scattering instrument where signal averaging of 0.1 to 10 seconds is typically used.

It is important to note that in all of the prior art, the noise reduction method has focused on the laser output power itself, and does not directly utilize filtering, signal averaging of the detected signal or mathematical ratioing of the signal and laser monitor. Because of our concern with the over-all performance of the whole light scattering instrument which need determine only the ratio of scattered light to incident laser power, it is possible to allow, and even encourage fluctuations in the laser output if the fluctuations can be effectively tracked or removed after signal detection. Our approach to the problem is to shift the frequency of the mode hopping noise above the passband of the signal processing filters in the detection system. Thus the laser drive modulation, matched signal averaging filters, and the ratioing of scattering to incident light are all essential parts of this invention.

BRIEF DESCRIPTION OF THE FIGURES

FIGS. 3A and 3B show the effect of the noise reduction method on laser power mode hopping noise induced by temperature drift while

BRIEF DESCRIPTION OF THE INVENTION

The object of our invention is to permit the use of compact solid state laser sources in light scattering instruments. Similar techniques could be applied to other types of laser sources exhibiting high frequency fluctuations, as would be evident to those skilled in the art. Traditional light scattering instruments, or photometers, measure scattered light at one or more angles and may be used with light sources of slowly varying non-constant output because they generally monitor also the intensity of the incident light source by beam splitters, or other means. Because of mode hopping caused by reflected and/or stray light reentering the laser as well as mode hopping caused by temperature variations, laser, and particularly solid state diode laser outputs may on occasion undergo rapid intensity fluctuations or stepwise changes that cannot be adequately averaged and monitored by the standard techniques. For example, a change in mode structure may not only change the total output power of the laser, but also change the ratio of laser monitor power to power incident on the sample. These problems are particularly serious with very dilute solutions of small molecules where the scattered light is weak, and accurate subtraction of stray light is required, since the stray light may change with a change in laser modes. Our invention addresses this point by modulating the laser intensity in such a manner that the resulting signal can be effectively filtered and measured with great accuracy, both in the laser monitor and in the scattered light detectors. By modulating the laser drive rapidly to scan through all available mode configurations, stepwise changes in the averaged signals are eliminated. The resulting slow changes can then be tracked accurately and an accurate ratio of scattered to incident light can be determined. In lasers with external optics, other forms of modulation may be used to alter the mode structure, such as motion of the laser cavity mirrors, or optical phase modulation in the laser cavity.

Thus our invention reduces the effects of the mode-hopping on the measured light scattering ratio. This invention is to be contrasted with prior art that seeks to quiet the optical signal produced by the laser itself. Even though the modulated laser output contains rapid power fluctuations, electronic averaging of the modulated laser output removes the sudden sharp changes in power level and leaves only a small, slow, smooth change in average laser power. This slowly drifting average laser power level is measured through the use of a split beam monitor. Light scattering signals can be similarly averaged to produce a smooth, slowly varying signal, so that ratios can be determined of the scattered light signal at each angle monitored relative to the laser power signal as required for the light scattering measurement.

DETAILED DESCRIPTION OF THE INVENTION

Figure 1:
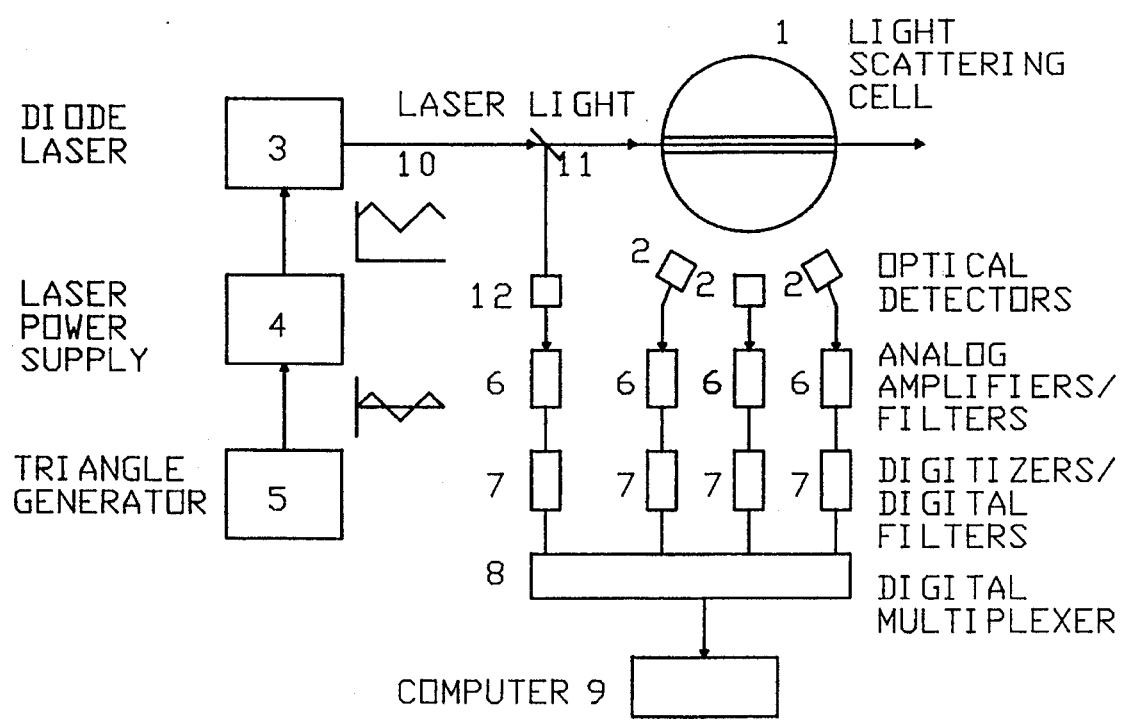
FIG. 1 shows a block diagram of the stabilization method as it forms part of a light scattering detection system of the preferred embodiment of the invention.

FIG. 1 shows the configuration of a light scattering measurement performed in a light scattering photometer using a flow through sample cell 1 surrounded by a plurality of collimated scattered light detectors 2. Said light scattering detectors, as well as detectors used to monitor the illumination source/laser described below, are generally photodiodes, of a hybrid form incorporating linear amplifiers. Historically, photomultiplier tubes had been used for this purpose, though their quantum efficiency at the red wavelengths emitted by many types of laser diodes is very poor. The sample is illuminated by a solid state laser 3 whose controlled current power supply 4 is modulated by a wave generator 5. Said solid state laser is generally combined with an optical collimation lens means so that the laser will produce a collimated output commonly referred to as a beam 10. In the preferred embodiment of our invention the wave generator produces a triangular wave. The cell may be of a design similar to that described in U.S. Pat. No. 4,616,927, though any other type of cell, such as a rectangular or cylindrical cell, which is illuminated by a solid state laser could be used in a photometer with the same laser modulation method. The individual scattered light detectors each are provided with amplifiers including analog filters 6. The signals generated thereby are digitized by individual digitizer circuits 7 containing digital filters to suppress higher frequency signals incompatible with the experimental conditions to be measured. The analog and digital filters are typically low pass filters chosen to block the frequencies generated by modulation of the laser, while passing the frequencies typical of the light scattering signals to be measured. Of course, an analog multiplexer may be used to switch the signals into a single analog to digital converter to achieve the same final result. The digital signals thus processed may then be multiplexed by a digital multiplexer 8 for transmission to a computer 9 over said computer's serial port. Part of the laser beam 10 is directed by a beam splitter 11 into a laser monitor 12 with its associated similar electronic components 6 and 7.

Because the laser diode drive current is a critical parameter for controlling laser power and preventing damage to the diode, conventional design often uses a current regulated power supply. Of course, a Norton equivalent voltage source and current limiting resistor may be used also. A convenient way to modulate the laser current, and thus "sample" the available mode states is to add a periodic waveform voltage to the reference voltage of the power supply, so that the laser current varies with the periodic waveform. A triangle waveform is preferred, because it spends equal time at each current level, though other waveforms may be used as well. In the preferred embodiment, the peak current would be limited to a safe value for the laser diode by a single control, and an independent control would allow the adjustment of the degree of modulation. The depth of modulation can then be adjusted for the best resultant smoothing of mode-hopping noise. The minimum drive current for which lasing occurs is referred to as the threshold current. Laser light output increases rapidly as the drive current is raised above the threshold level. In practice we have found that peak-to-peak modulation of about 15% of the current above threshold is generally adequate to obtain smoothing though values up to about 50% would function also. For example, a diode with threshold current of 40 ma, operated at 60 ma, requires 0.15×(60–40)=3 ma peak-to-peak modulation to achieve a resultant smoothing. The maximum laser diode drive current is limited to less than an instantaneous peak value that would cause permanent damage to the laser. In practice, the laser could be operated with average current very close to the instantaneous maximum. Thus any modulation scheme involves spending some time at lower drive currents, and results in a lower average output power. It is an advantage of the preferred embodiment of our approach that only a 15% modulation is required, since this results in only a small loss of average power output. The optimum frequency of modulation depends to some degree on the system. For example, for the particular photometer configuration of the commercially sold miniDAWN® system made by the Wyatt Technology Corporation incorporating a 20 mW InGaAlP laser, for example Toshiba model TOLD 9140 operating in single transverse mode at 690 nm, we found a modulation frequency of 150 Hz to be convenient and effective. This frequency was high enough to be effectively filtered by the instrument's analog and digital filters, and low enough to sample the longitudinal mode-hopping effectively. Ideally, the modulation frequency should be between 10 and 1000 times greater than the frequency of the measured scattered light signal. The laser output beam used for light scattering instruments is generally linearly polarized although such polarization is not essential to our invention. In the preferred embodiment of our invention in a light scattering measurement the incident light should be vertically polarized relative to a horizontal plane containing the scattered light detectors.

Figure 2A:
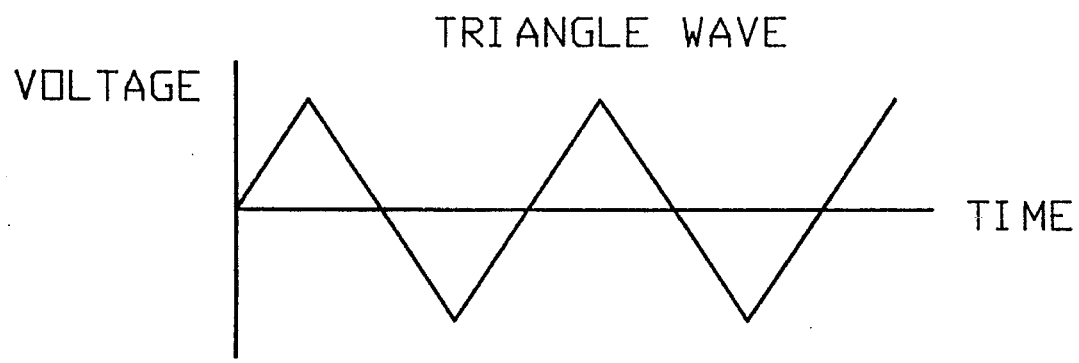
FIGS. 2A and 2B show respectively the form of the applied voltage and resulting laser current of a triangular wave modulation of the laser driving current.
Figure 2B:
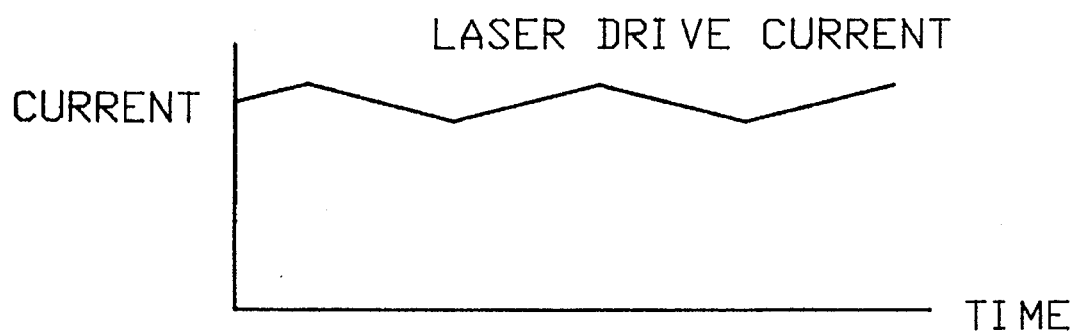

FIGS. 2A and 2B respectively show the applied voltage and resulting laser drive current of the form of a triangular wave used, in the preferred embodiment of this invention, to modulate the laser output power. The frequency of measurement of a typical light scattering signal produced during the passage of a sample eluant through the optical flow cell of a light scattering detector is the order of a few Hertz or less. On this basis, it has been found that a modulation frequency of the order of 150 Hz is suitable to permit sufficient smoothing out of the laser power irregularities produced by the mode-hopping. In the event that a higher frequency scattering signal measurement were required, the laser modulation frequency should be increased accordingly. As stated earlier, a role of thumb would suggest that, the modulation frequency selected should be chosen one to three orders of magnitude greater than the detection frequency. For typical light scattering measurements made in conjunction with a liquid chromatography separation of polymeric samples, a frequency between 50 and 5000 Hz will suffice. We have found that each type of laser/detection configuration may require a different optimal frequency and amplitude for the modulation of the laser current. Following the examples presented below, it will be a relatively easy matter for those skilled in the art of light scattering instrumentation to identify the optimal modulation frequency and amplitude for most types of laser sources for which mode-hopping induced noise affects the subsequent scattering measurements. Although the preferred embodiment of this invention includes a triangular wave modulation of the laser current supply, it should be evident to those skilled in the art that other forms may well be satisfactory. Such would include simple sine waves, saw tooth waves, and any other periodic or random waveforms that would sweep and thereby sample all modes expected to contribute to the output power fluctuations.

Figure 3A:
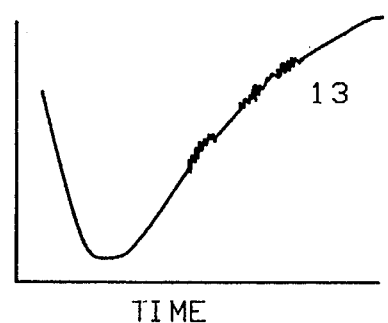
Figure 3B:
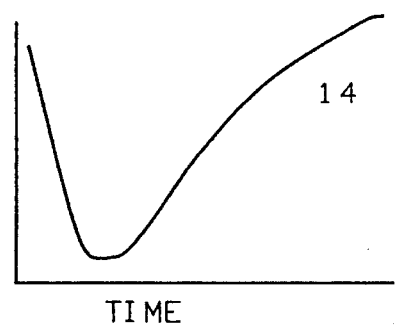
Figure 3C:
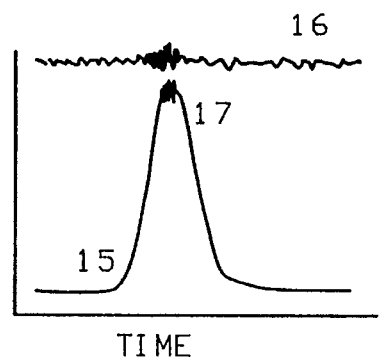
FIGS. 3C and 3D show the effect of the house reduction method on laser power mode hopping, and on noise induced by reflected light from a light scattering sample in parts C and D.
Figure 3D:
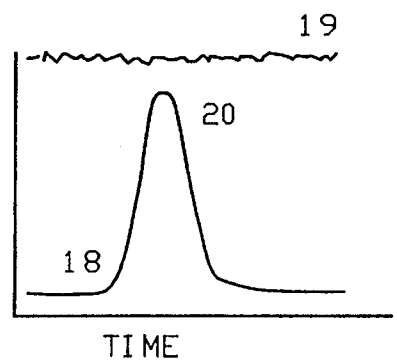

FIGS. 3A to 3D show laboratory data collected with the triangular wave modulation of the preferred embodiment. The data labeled 13 of FIG. 3A show the unmodulated laser power output produced by heating the diode laser momentarily with a heat gun and then allowing it to cool. After using a 15% modulated triangular laser current at 150 Hz, the result 14 of FIG. 3B is obtained. Note that the smooth long term variation in the laser power is of no import to the typical light scattering measurement since the scattering signals are normalized by dividing by the beam monitor signal. Such normalization is usually performed by digitizing each analog scattered light and laser monitor signal by means of an analog to digital converter, filtering the digital data using a digital signal processor, storing such digitized and filtered values in a computer means and then calculating the required ratio by dividing each so-digitized scattered light signal by the digitized laser monitor signal to obtain thereby a digitized ratio for each scattered light signal. Alternatively, said smoothed signal ratios may be generated by analog division means by which the output ratio signal is itself an analog value. Other variations of this general method, such as using the laser monitor signal to regulate the average laser power, will occur to those skilled in the art. When a narrow polystyrene sample is injected into the solvent flowing through a photometer system such as shown in FIG. 1, the resulting unmodulated scattered 90° light signal 15 shown in FIG. 3C is obtained with a corresponding output laser power 16 shown in FIG. 3C. Note the noise at the peak 17 of FIG. 3C due to mode hopping caused by the reflection of scattered light back into the laser. With laser modulation, the corresponding averaged scattering signal is shown at 18 and laser power 19 of FIG. 3D. The peak data 20 shown of FIG. 3D do not exhibit the peak data irregularities of 17 shown in FIG. 3C. Note that the light scattering signal for the unmodulated laser current has affected the laser output power itself by scattering some light back into the laser and/or by changing the phase of reflected light.

Figure 4:
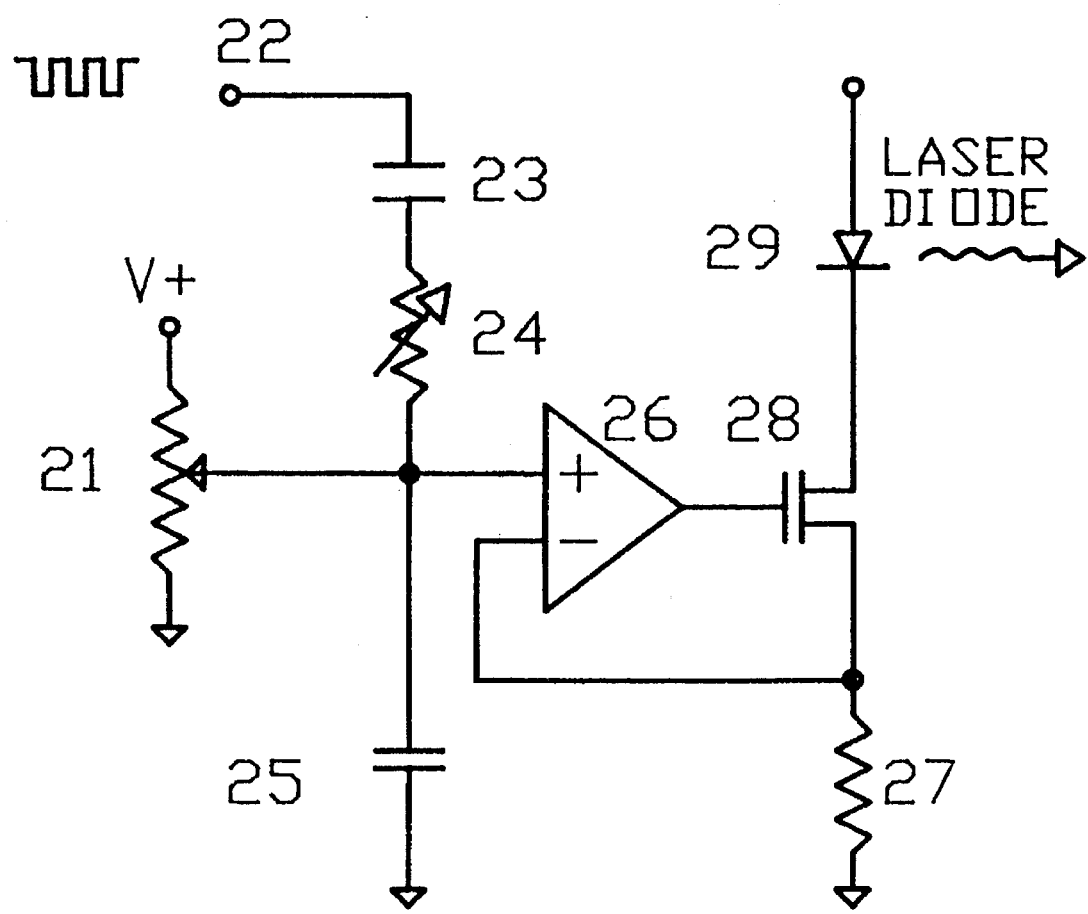
FIG. 4 shows the circuit diagram of a typical implementation of the laser stabilization method in a power supply for a solid state InCaAlP laser operating at 20 mW peak power at 690 nm.

FIG. 4 shows a schematic of the preferred embodiment of a circuit to provide modulated current to a laser diode as used in a light scattering photometer illustrated by FIG. 1. A potentiometer 21 delivers an adjustable DC voltage to the non-inverting input of an operational amplifier, or opamp, 26. The opamp controls the gate of a field effect transistor 28 which in turn controls the current to the laser diode 29. The negative feedback for the current control opamp is provided by the voltage generated across the series resistor 27. The modulation is created by AC coupling a square wave voltage 22 through coupling capacitor 23 and adjustable coupling resistor 24 to the current control input. The filter action of resistor 24 and integrating capacitor 25 converts the square wave input into a good approximation of the desired triangle wave. The AC coupling of the modulation allows independent control of the average DC laser current by means of potentiometer 21 and the modulation amplitude by resistor 24.

Now whereas we have discussed herein the preferred means by which intrinsically noisy laser sources may be used effectively in light scattering instruments and measuring devices, it will be obvious to those skilled in the art that there are numerous variations possible to the preferred embodiments of our invention that we have described and that all such obvious variations in form, amplitude, and frequency of modulation are included in the full scope of this invention.

Therefore, we claim:

1. A method for controlling a laser source, which is inherently noisy due to mode hopping instabilities, for use in a light scattering measurement comprising the steps of:

a) modulating the laser drive current at a frequency approximately 10 to 1000 times greater than the frequency of measurement of the scattered light signals and with a maximum amplitude less than the peak current level of the laser;

b) splitting a fraction of the laser output beam so-produced and detecting said split fraction with a light sensitive monitor detector to obtain thereby a representative measure of said output beam power;

c) averaging the signal produced by said monitor detector with a signal averaging filter selected to smooth the power fluctuations due to said modulation;

d) detecting the light scattered by a sample illuminated by said modulated laser beam at one or more angles and averaging each said detected scattered light signal at each said angle with a signal averaging filter approximately equal to the signal averaging filter selected to smooth said power fluctuations of said monitor detector, each said signal averaging filter smoothing the detected scattered light fluctuations due to said modulation of said illuminating laser beam;

e) dividing the so-smoothed scattered light signals by the similarly smoothed laser monitor signal to produce an output ratio of the light scattered by said sample to the light incident thereon for each of said angles measured.

2. The method of claim 1 where said laser source is a solid state laser diode.

3. The method of claim 1 where said modulation is between 50 and 5000 Hz.

4. The method of claim 1 where said detected laser monitor and scattered light signals are digitized and said output ratios are calculated by computer means.

5. The method of claim 1 where said output ratios are obtained by means of an analog division of each of said scattered light signals by said laser monitor signal.

6. The method of claim 1 where said laser drive current is modulated by a triangular waveform.

7. The method of claim 1 where the peak-to-peak modulation of said laser drive modulator is less than 50% of the current above threshold.

8. The method of claim 1 where the modulation frequency of said laser drive modulator is between 10 and 1000 times greater than the band pass frequency of the measured scattered light signals.

9. The method of claim 1 where said laser output beam is linearly polarized.

10. The method of claim 2 where said laser operates at a wavelength of about 690 nm.

11. The method of claim 1 where said detectors are photodiodes.

12. The method of claim 1 where the minimum amplitude of said modulated laser drive current is greater than the threshold drive current required to initiate lasing.

13. The method of claim 1 where the peak to peak modulation of said laser drive current modulator is approximately 15% of the current above threshold.

14. The method of claim 1 where said laser drive current modulation is approximately 150 Hz.

15. An illumination system, for use in a light scattering instrument, incorporating a laser light source producing a collimated beam which is inherently noisy due to mode hopping instabilities, comprised of:

a) laser means producing said collimated beam subject to said mode hopping instabilities;

b) modulation means capable of modulating laser drive current at a frequency approximately 10 to 1000 times greater than the frequency intended for measurement of the scattered light signals and with a maximum amplitude less than the peak current level of said laser;

c) means for splitting a fraction of said collimated laser output beam so-produced and means for detecting said split fraction with a light sensitive monitor detector means producing thereby a monitor signal representative of said output beam power; and d) monitor signal averaging filter means to smooth fluctuations in said monitor signal due to said modulation of said collimated laser output beam, said signal averaging filter means being approximately equal to the signal averaging filters used in said light scattering instrument.

16. The illumination system of claim 15 where said laser means is a solid state diode laser.

17. The illumination system of claim 15 where said modulation means modulates said laser drive circuit between 50 and 5000 Hz.

18. The illumination system of claim 15 where said light sensitive monitor detector means is a photodiode.

19. The illumination system of claim 15 where said laser drive current modulation means modulates said laser drive current to produce a triangular waveform.

20. The illumination system of claim 15 where the amplitude of the peak-to-peak modulation of said laser drive modulator is less than 50% of the current above threshold.

21. The illumination system of claim 15 where the modulation frequency of said laser drive modulator is between 10 and 1000 times greater than the band pass frequency of the measured scattered light signals.

22. The illumination system of claim 15 where said laser produces a linearly polarized output beam.

23. The illumination system of claim 16 where the laser operates at a wavelength of about 690 nm.

24. The illumination system of claim 15 where said modulation means produces a minimum laser drive current greater than the threshold drive current required to initiate lasing.

25. The illumination system of claim 15 where said modulation means produces a peak to peak modulation of said laser drive current of approximately 15% of the current above threshold.

26. The illumination system of claim 15 where said monitor signal averaging filter means is comprised of analog to digital conversion means to convert said monitor signal, digital storage means to store such digitally converted signals, and digital signal processing means to process and average said stored digitally converted signals.

* * * * *